United States Patent [19]

DeVroom

[11] 4,428,383

[45] Jan. 31, 1984

[54] MANIFOLD FOR MONITORING HEMODYNAMIC PRESSURE

[75] Inventor: William A. DeVroom, Glendora, Calif.

[73] Assignee: American Hospital Supply Corporation, Evanston, Ill.

[21] Appl. No.: 310,016

[22] Filed: Oct. 13, 1981

[51] Int. Cl.³ .............................................. A61B 5/02
[52] U.S. Cl. ................................... 128/748; 604/248; 137/883
[58] Field of Search ............... 128/748, 760, 673–675, 128/670, 672, 656; 604/51–53, 246–250, 322; 137/883

[56] References Cited

U.S. PATENT DOCUMENTS

| | | | |
|---|---|---|---|
| 2,954,028 | 9/1960 | Smith | 604/250 X |
| 3,122,136 | 2/1964 | Murphy, Jr. | 128/673 |
| 3,154,102 | 10/1964 | Harris | 137/883 |
| 3,477,469 | 11/1969 | Paley | 137/883 |
| 3,610,228 | 10/1971 | Temkin | 128/748 |
| 3,678,960 | 7/1972 | Leibinsohn | 604/248 X |
| 3,834,372 | 9/1974 | Turney | 128/760 X |
| 4,177,835 | 12/1979 | Paley | 137/883 |
| 4,267,835 | 5/1981 | Barger et al. | 604/250 |
| 4,300,572 | 11/1981 | Knighton | 604/248 X |
| 4,342,218 | 8/1982 | Fox | 128/673 X |

FOREIGN PATENT DOCUMENTS 2357489 5/1974 Fed. Rep. of Germany ...... 128/674

OTHER PUBLICATIONS

Wilkins et al., "Arterial Pressure Waveform Recording: A Clinical System"; *Bio-Med. Eng.;* vol. 7, No. 7, 8/72, pp. 309–312.

Primary Examiner—Lee S. Cohen
Assistant Examiner—Angela D. Sykes
Attorney, Agent, or Firm—Roger A. Williams

[57] ABSTRACT

A manifold assembly is provided for monitoring hemodynamic pressures. The manifold assembly comprises a base having first, second and third flush valves mounted thereon. A first three port stopcock is also mounted on the base having one of its ports in fluid flow communication with the first flush valve. One of the ports is in fluid flow communication with an arterial catheter and one of the ports is in fluid flow communication with a pressure monitoring means for determining arterial pressure. A first T-connector is fastened to the second flush valve. A second T-connector is fastened to the third flush valve. A second three port stopcock is mounted on the base with one of its ports in fluid flow communication with the second flush valve through the first T-connector. One of the ports of the second three port stopcock is in fluid flow communication with the third flush valve through the second T-connector.

16 Claims, 4 Drawing Figures

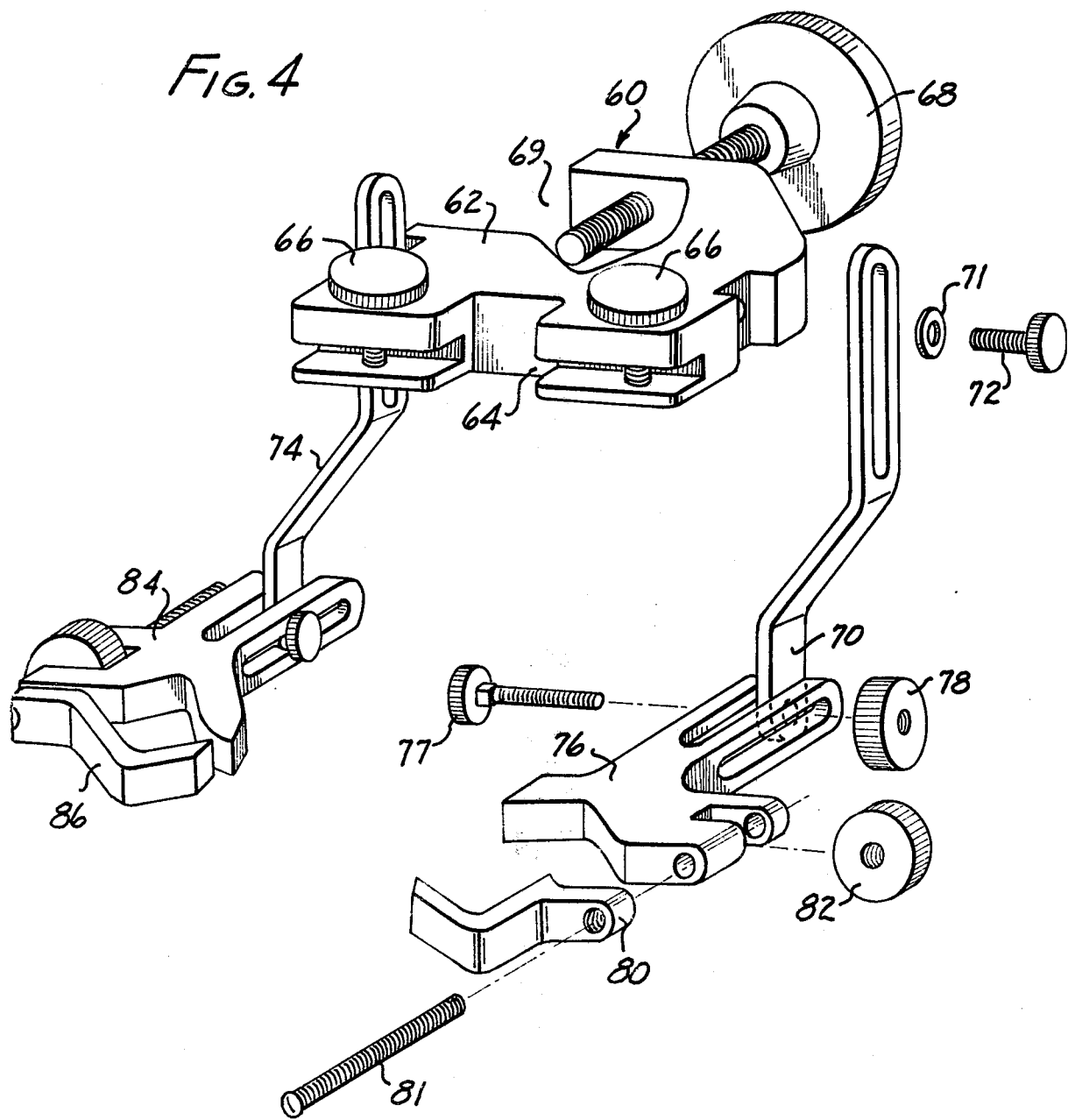

MANIFOLD FOR MONITORING HEMODYNAMIC PRESSURE

BACKGROUND OF THE INVENTION

This invention relates to medical appliances and more particularly to a manifold assembly for controlling flow of fluid and providing for monitoring of hemodynamic pressures.

Manifold assemblies have been provided in the past for medical applications and when not available many arrangements for manifolds have been quickly assembled from various available parts for particular applications. The assembling of manifolds is undesirable as many connections need to be made and time is required for assembly. Some preformed manifolds have been provided such as those shown in U.S. Pat. Nos. 3,477,469 and 4,177,835. The manifolds described in each of these patents merely are arrangements of three-way stopcocks which in the former is made of stainless steel, while in the latter is constructed of plastic.

Stopcock manifolds, typically consisting of three or five, three-way stopcock valves in series, have been used for continuous and intermittent monitoring of multiple invasive hemodynamic pressure lines in hospital intensive care units and coronary care units. Such manifolds have also been used in operating rooms and cardiac catheterization labs.

Manifolds have served a multitude of functions in a centralized fluid path valving network as the control center for hemodynamic monitoring systems.

In spite of major advantages to overall system control and function for multiple hemodynamic pressure lines and attendant patient handling, the use of stopcock manifolds has not been well received in many areas such as intensive care units and coronary care units. The poor reception for such stopcock manifolds has been due to high staff turnover, complex training requirements, confusion in the use of stopcocks in series and manifold connection setups, sterility concerns and assembly time.

It would be desirable to have a manifold designed to provide a convenient and simple device to replace the presently used stopcock manifolds which have many connecting arrangements and use and which are confusing to nurses and technicians not trained in each particular setup for the stopcock manifolds. It would also be desirable to have a manifold design which could reduce assembly time, reduce the potential for contamination and enhance user interpretation of the status of the cardiac pressure monitoring system.

SUMMARY OF THE INVENTION

The invention herein relates to a manifold assembly for use in monitoring hemodynamic pressures. The manifold assembly herein is easy to operate and connect to pressure lines being used to enable the monitoring of arterial pressure, right atrial pressure, pulmonary arterial pressure, left atrial pressure and central venous pressure.

The manifold assembly herein comprises a base having a first, second and third flush valves mounted thereon. A first three-port stopcock is mounted on the base with one of the ports in fluid flow communication with the first flush valve. One of the ports of the first three-port stopcock is in fluid flow communication with an arterial catheter and the remaining port is in fluid flow communication with a pressure transducer for monitoring arterial pressure. A first T-connector is interconnected with the second flush valve. A second T-connector is interconnected to the third flush valve. A second three-port stopcock is mounted on the base with one of the ports in fluid flow communication with the second flush valve through the first T-connector. One of the ports of the second three-port stopcock is in fluid flow communication with the third flush valve through the second T-connector. The remaining port on the stocock is in fluid flow communication with a second pressure transducer.

The three flushing valves are in fluid flow communication through a trifurcated IV set with an IV solution source.

Additional features of the invention will be apparent from the following detailed description and accompanying drawings wherein the preferred embodiments are set forth.

BRIEF DESCRIPTION OF THE DRAWINGS

FIG. 4 is a perspective, partially exploded view of a mounting bracket for use in mounting the manifold assembly herein to a support.

DETAILED DESCRIPTION OF THE INVENTION

Figure 1:
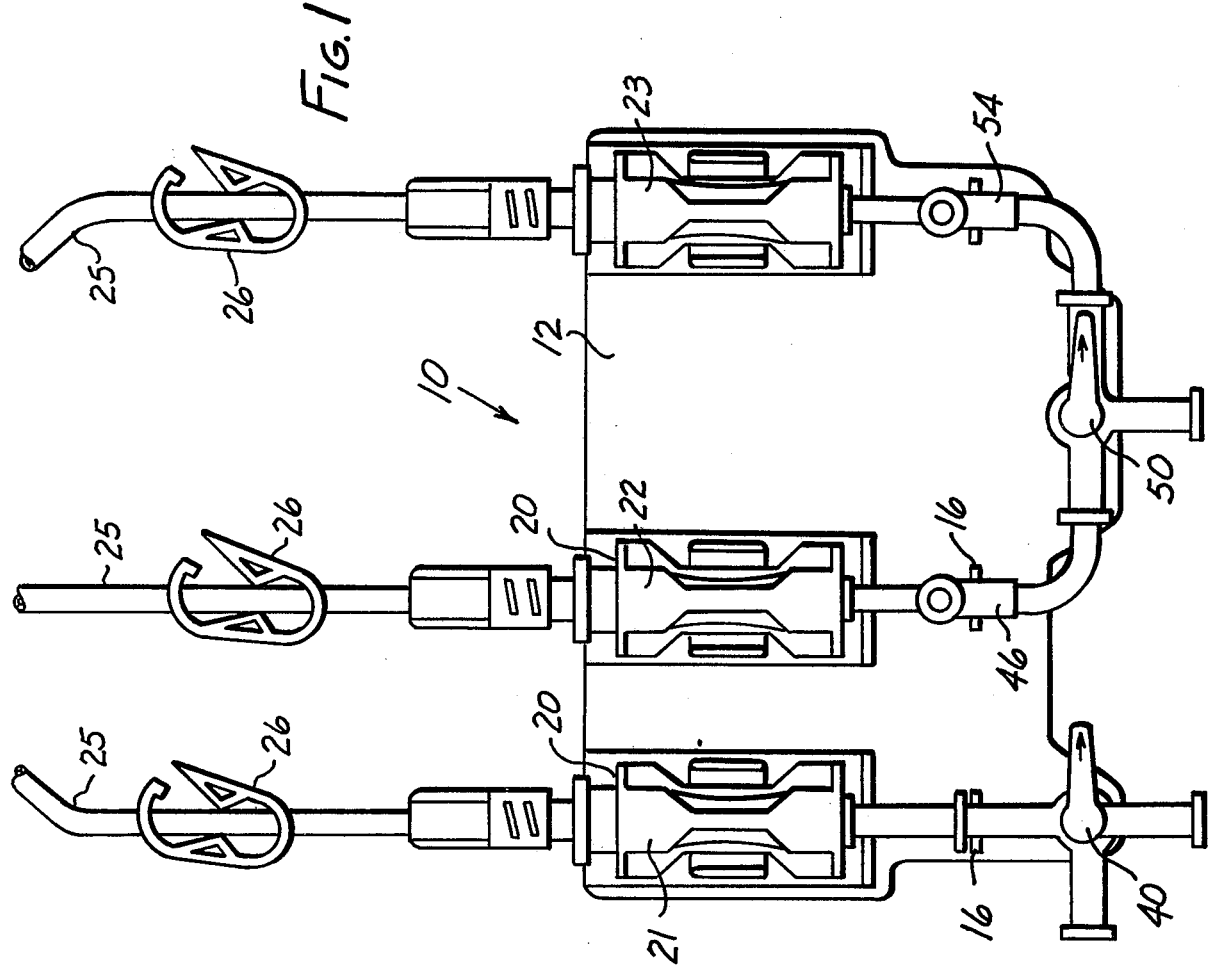
FIG. 1 is an elevational view of one embodiment of a manifold assembly according to the invention.

The manifold assembly herein is described with regard the FIGS. 1 through 4. With regard to FIG. 1, a manifold assembly 10 is shown having a base 12 which is a substantially flat, planar surface having apertures 14. Cradles 16 can be provided on the base for mounting and supporting flushing valves 20.

A planar surface forming a mounting bracket 18 extends away from the base. The mounting bracket can extend at any suitable angle from the base, such as at a 90° angle as is shown. The mounting bracket 18 provides for attaching the manifold device to a support, such as the tubular stand support shown in FIG. 2. The base and mounting bracket can be constructed of any suitable material, such as plastics, including polysulfones and polycarbonates.

Mounted on the base are 3 flushing valves 20. Acceptable flushing valves can be flushing valves which provide for a fast flushing of fluid therethrough to prevent obstruction and provide for flushing of air bubbles from the system. In the preferred embodiment, flushing valves are utilized which provide for fast flushing. Suitable flushing valves are described in U.S. Pat. No. 4,267,835, the entire disclosure of which is incorporated herein by this reference.

Basically, the flushing valve comprises an elastically distortable tube with a noncircular outer surface that includes a force concentrating section. A restrictor in the tube combines with the tube to form a restricted passage means in the form of a fixed size bore extending through the restrictor and having a predetermined flow rate therethrough. The tube can be distorted by application of a force to the force concentrating section of the tube's outer surface to temporarily form a flush passage in the valve. The flush passage has a substantially faster flow rate during the application of such a force than the restricted passage. The tube is adapted to close the flush passage upon removal of such a force from the force concentrating section. The force can be applied to the force concentrating section by squeezing the flushing actuators 24 on each of the flushing valves 20.

The manifold assembly herein provides a base for a plurality of such flushing valves 20. In a particular working embodiment the manifold device included a first flushing valve 21, a second flushing valve 22 and a third flushing valve 23 as is shown in the accompanying drawings. Such a manifold assembly having three flushing valves has utility as a cardiac pressure monitoring system, which can be used to monitor arterial, pulmonary artery, and right atrium/central venous pressures. A manifold assembly basically including the right hand portion and two flushing valves of the manifold assembly of FIG. 1 can be used for monitoring venous pressures.

The inlet ports of the flushing valves are connected through a trifurcated intravenous set to an IV solution container 38. The trifurcated IV set comprises tubing 25 attached to each of the inlet ports of the first, second and third flushing valves. Positioned along the tubing 25 are clamps 26 capable of closing the tubing 25 to fluid flow. The tubing 25 is connected to a three-way connector 28 which splits the IV solution flowing from the IV container 38 into three fluid paths. The three-way connector 28 is in turn connected to tubing 30 having a clamp thereon, such as a roller clamp 32 for selectively preventing or allowing fluid flow through the tubing 30. The tubing 30 can be connected to a drip chamber 34 which in turn is connected through a suitable needle 36 to the IV container 38.

Connected to the outlet port of the the first flushing valve 21 is a first three-way stopcock 40 having three ports. One of the ports of the three-way stopcock is connected to the outlet port of the first flushing valve. A second port of the three-way stopcock is connected through tubing 42 to an arterial catheter 43. The tubing 42 and other tubing herein later described can be any high pressure tubing suitable for monitoring hemodynamic pressures. Positioned along the tubing 42 can be a stopcock 41 which provides for the introduction of medicaments or which can be closed and opened selectively.

Connected to the third port of the first three-way stopcock is a first pressure transducer 44. Such a pressure transducer can be a pressure transducer dome capable of converting pressure sensed within the flow passageway to an electrical signal. Many of such pressure transducers are commercially available and such commercially available pressure transducers can be utilized in the system herein.

Figure 2:
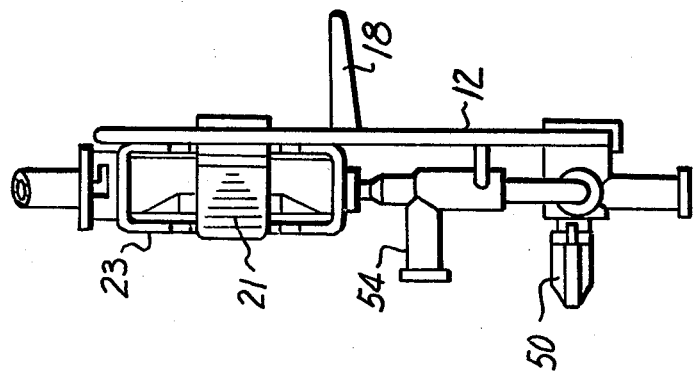
FIG. 2 is a side elevational view of the embodiment of FIG. 1.

Connected to the outlet port of the second flushing valve 22 is a first T-connector 46. One of the ports of the first T-connector is connected through high pressure tubing 47 to one of the lumens of a double lumen catheter. A suitable double lumen catheter can be a Swan-Ganz catheter which is a trademark of American Hospital Supply Corporation for a double lumen catheter used in detecting pulmonary artery and central venous pressure. When such a Swan-Ganz catheter is utilized, the tubing 47 can be connected to the distal port of the catheter to enable monitoring of pulmonary artery pressure. The tubing 47 can be interconnected to the distal port of the Swan-Ganz catheter through a stopcock arrangement as is shown in FIG. 2, which provides for the administration of medicaments, the collection of blood samples, or for selectively opening and closing of the passageway.

Connected to the remaining port of the first T-connector 46 is a second three-way stopcock 50 having three ports. One of the ports of the second three-way stopcock is connected to the first T-connector. A second port of the second three-way stopcock is interconnected to a second pressure transducer 52, which second pressure transducer can be a pressure transducer dome interconnected to provide for converting the pressure in a fluid within the dome to an electrical output.

The third port of the second three-way stopcock is interconnected to a second T-connector 54. The second T-connector is interconnected to the outlet port of the third flushing valve. The remaining port of the second T-connector is connected to high pressure tubing 55. The high pressure tubing 55 is interconnected to the remaining lumen of the double lumen catheter. For example, for a Swan-Ganz catheter the tubing 55 is interconnected with the proximal port 56 of such a Swan-Ganz catheter which provides for monitoring right atrium/central venous pressure. As with the other tubing connecting to the catheters inserted within the body of a patient, the tubing 55 can be interconnected through a suitable stopcock arrangement.

Figure 3:
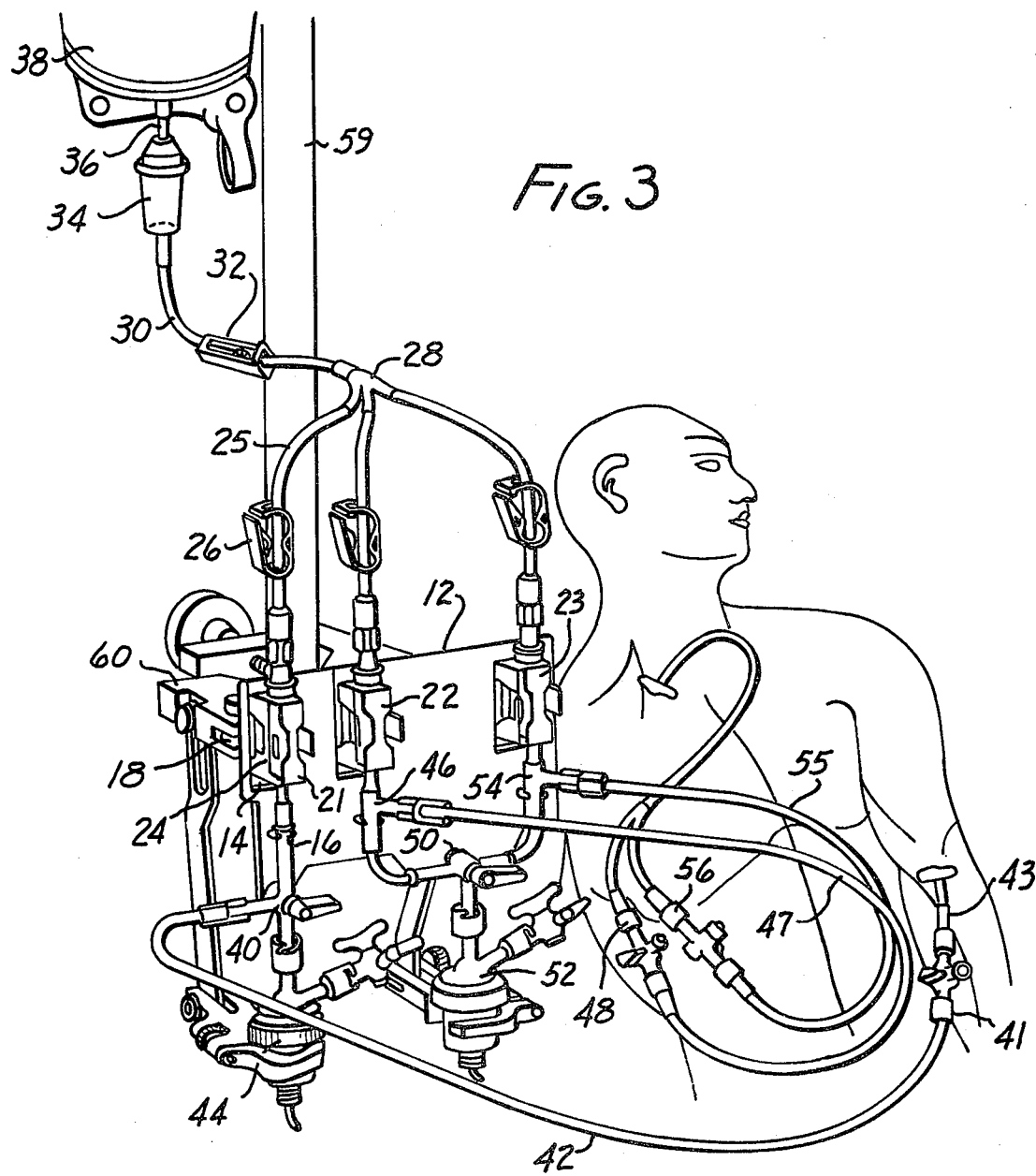
FIG. 3 is a perspective view showing the utility of the manifold monitoring system herein.

As shown in FIG. 3 the hemodynamic montoring system herein can be mounted on a vertically extending support 59 using a manifold mounting clamp 60. The manifold mounting clamp is shown in a partially exploded perspective view in FIG. 4.

With regard to FIG. 4, the manifold mounting clamp 60 has a body 62 that is generally a planar surface. Within the body is at least one slot 64 for receiving the mounting bracket 18 of the manifold assembly 10. Manifold holding screws 66 extend through the body of the manifold mounting clamp into the slot 64 for securing the mounting bracket of the manifold assembly to the manifold mounting clamp.

Attached to the manifold mounting clamp is a knob assembly 68. The knob assembly extends through the body of the manifold mounting clamp into a notch or recess 69. The recess 69 is of sufficient size for engaging the vertical support 59. The knob assembly 68 is threaded and can be rotated to tighten against the vertical support 59 to secure the manifold mounting clamp at the desired elevation along the support Also attached to the body are a pair of arms which generally extend downwardly from the body. The pair of arms comprise a first extension arm 70 and a second extension arm 74 both having slots therein for providing height adjustability of the arms. The first and second extension arms are secured to the body using a washer 71 and threaded lock screw 72.

Attached to the ends of the first and second extension arms are first and second transducer supports 76 and 84 respectively. With regard to the first transducer support 76 (shown in exploded view), it can be attached to the first extension arm through a carriage bolt 77 and thumb nut 78 which provide adjustability to the first transducer support.

A transducer arm assembly 80 is adjustably fastened to the first transducer support 76. The transducer arm assembly can be secured to the first transducer support through a bolt 81 and a thumb nut 82. The transducer arm assembly 80 and first transducer support cooperate to engage and support the second pressure transducer 52. In a similar fashion, the second transducer arm assembly and the second transducer support cooperate to engage and support the first pressure transducer 44.

The second transducer support 84 and second transducer arm assembly 86 are identical in arrangement to the first transducer support and first transducer arm assembly 80.

When the manifold device is used for hemodynamic monitoring, the following discussion regarding FIG. 3 describes a typical monitoring system. The manifold assembly 10 can be attached to a pressurized IV solution and connected to the patient through suitable high pressure monitoring lines 42, 47 and 55. The IV solution is connected such that the solution flows continuously to maintain patency of the pressure line. To fill the pressure lines initially or for flushing the catheters, the manifold assembly can be fast flushed by squeezing on the appropriate actuator 24 on the appropriate flushing valve 20.

For administering an IV solution to a patient using the manifold assembly herein, heparin can be added to the solution in the IV reservoir 38 which can be a collapsible IV bag. All air from the IV solution reservoir 38 is extracted. The roller clamp 32 is closed and any protective cap removed from the spike of drip chamber 34. The spike is inserted into the outlet port of the IV reservoir which is suspended to permit drainage of the reservoir into the hemodynamic monitoring system.

The pressure transducers, such as disposable pressure transducer domes, are attached to the first and second three-way stopcocks. It is ensured that both transducers are connected at about the same elevation so as to be at the same hydrostatic pressure level.

The roller clamp 32 is opened and each clamp 26 on the three branched sections is opened. The IV solution is allowed to fill each continuous flushing valve 20 and each monitoring fluid path channel by gently squeezing on each actuator. The port on the first three-way stopcock and the two ports on the first and second T-connectors which connect with the pressure monitoring lines are also filled. These ports can be capped with dead end protectors until ready to attach the pressure monitoring lines.

The arterial monitoring side fluid path channel is filled by turning the first three-way stopcock handle to allow flow through all three ports of the stopcock. This arterial side stopcock can be rotated a full 360° to allow all ports to be opened or to selectively close any desired port. Generally, the stopcock handle is always over a closed port to indicate which port of the three-way stopcock is closed.

The venous monitoring side fluid path channels are filled by first filling the pulmonary artery channel and transducer by squeezing the actuator on the second flushing valve 22 with the stopcock handle of the second three-way stopcock turned to the right, closing off the right atrium/coronary venous pressure (CVP) fluid path. This venous side stopcock can only be rotated through the lower half 180° in the conventional manner. The second three-way stopcock handle is then rotated to the down position to close off the transducer port and fill the channel with IV solution between the pulmonary artery channel and the right atrium/CVP port. It is ensured at this time that all air bubbles are removed in the process. Finally, the handle on the second three-way stopcock is turned to the left, closing off the pulmonary artery fluid path and filling the right atrium/CVP channel and second pressure transducer. This second pressure transducer on the venous side is used for monitoring either the pulmonary artery or right atrium/CVP pressure depending upon which flow channel is selected.

All the fluid channels of the manifold assembly are filled until the IV fluid fills the transducer domes and appears at the ports of venting stopcocks provided on the transducer domes. The venting stopcocks are closed and each of the transducer domes are connected to pressure transducers using standard procedures.

The arterial line pressure tubing 42 is connected to a port of the first three-way stopcock. The pulmonary artery line pressure tubing 47 is connected to a port of the first T-connector 46. The right atrium/CVP line pressure tubing 55 is connected to a port of the second T-connector 54. The pressure tubing is then filled with the IV solution by opening stopcocks provided on the ends of such tubing. Prior to connecting the catheters, all air bubbles are eliminated from the system. It is generally recommended that stopcocks 41 used in the collection of blood samples be located as near to the catheter connection sites as practical to avoid withdrawal from the patient of a larger sample volume than needed and the subsequent flushing of a large internal fluid path area.

Each of the flushing valves is activated by squeezing the actuators until IV solution fills the respective pressure lines and forms a hemisphere at the catheter connection site. The catheter hub is then connected to the appropriate pressure line. Blood is flushed from the catheter by squeezing on the appropriate flushing valve actuator.

Generally, the desired flow rate will be approximately 2 to 4 milliliters per hour for typical patient use. If the continuous flow rate is not within the desired range, it can be adjusted by changing the IV solution pressure. Higher IV solution pressure increases the flow rate and lower IV solution pressure decreases the flow rate. An approximate reading of the total IV solution flow rate can be taken by noting the drops of solution within the drip chamber.

When the manifold assembly is attached and interconnected to a patient as above described, the arterial pressure can be determined directly from the reading taken by the first pressure transducer. The pulmonary artery pressure or the right atrium/CVP pressure can be monitored by selectively positioning the handle on the second three-way stopcock to provide for monitoring either the pulmonary artery or right atrium/CVP pressure with the second pressure transducer.

The manifold assembly herein provides consistent and convenient patient cardiac pressure monitoring care while reducing user set up time, training and sources of contamination. The manifold assembly herein provides the ability to continuously monitor two of three patient cardiac pressure monitoring lines and intermittently monitor the third line as desired. In a typical application, for example, cardiac pressure lines could be monitored from an arterial catheter and intermittently from the distal and proximal lumens of a double lumen catheter. The manifold design provides a built-in continuous flush function in preassembled components. The manifold assembly is simple to operate and maintain proper identification of the monitoring channels.

I claim:

1. A manifold assembly for monitoring hemodynamic pressures comprising:
   a base;

first and second flush valves mounted on the base;
a first T-connector in fluid flow communication with the first flush valve;
a second T-connector in fluid flow communication with the second flush valve;
a three port stopcock mounted on the base and having one of its ports in fluid flow communication with the first T-connector and one of its ports in fluid flow communication with the second T-connector.

2. A manifold assembly for monitoring hemodynamic pressures comprising:
a base;
first, second and third flush valves mounted on the base;
a first three port stopcock mounted on the base having one of the ports in fluid flow communication with the first flush valve;
a first T-connector fastened to the second flush valve;
a second T-connector fastened to the third flush valve;
a second three port stopcock mounted on the base having one of the ports in fluid flow communication with the second flush valve through the first T-connector and having one of the ports in fluid flow communication with the third flush valve through the second T-connector.

3. A manifold assembly as recited in claim 1 or 2 wherein the base comprises a substantially flat planar surface including mounting means for mounting the base to a support.

4. A manifold assembly as recited in claim 3 wherein the mounting means comprises a planar surface extending outwardly from the planar surface of the base.

5. A manifold assembly as recited in claim 2 further comprising a first pressure transducer attached in fluid flow communication to a second port of the first three port stopcock and a second pressure transducer attached in fluid flow communication to a second port of the second three port stop cock.

6. A manifold assembly as recited in claim 2 or 5 further comprising an arterial catheter attached in fluid flow communication with a third port of the first three port stopcock.

7. A manifold assembly as recited in claim 2 or 5 further comprising a double lumen cardiac catheter wherein the lumens of the catheter are provided to open into the pulmonary artery and right atrium and one of the lumens being in fluid flow communication with a port of the first T-connector and one of the lumens being in fluid flow communication with a port of the second T-connector.

8. A manifold assembly as recited in claim 2 further comprising a trifurcated intravenous set in fluid flow communication with the first, second and third flush valves.

9. A manifold assembly as recited in claim 8 wherein the trifurcated IV set comprises a needle having a lumen extending therethrough; a drip chamber connected to the needle; first resilient tubing connected to the drip chamber; a four port connector attached to the resilient tubing; second, third and fourth resilient tubing connected respectively to the remaining three ports of the four port connector and each connected to a flush valve.

10. A manifold assembly as recited in claim 9 further comprising a roller clamp on the first resilient tubing.

11. A manifold assembly as recited in claim 9 further comprising a clamp means on the second, third and fourth resilient tubing for selectively occluding such tubing.

12. A hemodynamic pressure monitoring system comprising:
a base;
first, second and third flush valves mounted on the base;
a first three port stopcock mounted on the base having one of the ports in fluid flow communication with the first flush valve;
an arterial catheter connected in fluid flow communication with one of the ports on the first three port stopcock;
a first pressure transducer means for determining arterial pressure connected in fluid flow communication with one of the ports on the first three port stopcock;
a first T-connector fastened to the second flush valve;
a second T-connector fastened to the third flush valve;
a second three port stopcock mounted on the base having one of the ports in fluid flow communication with the second flush valve through the first T-connector, having a port in fluid flow communication with the third flush valve through the second T-connector;
a second pressure transducer means in fluid flow communication with a port on the second three port stopcock for selectively determining either pulmonary arterial pressure or right atrial/central venous pressure depending upon opening the second three port stopcock to fluid flow; and
a double lumen catheter having a lead opening to one of the lumens connected in fluid flow communication to the first T-connector and having a lead opening to the other lumen connected in fluid flow communication to the second T-connector.

13. A hemodynamic pressure monitoring system as recited in claim 12 further comprising a trifurcated intravenous set in fluid flow communication with the first, second and third flush valves.

14. A hemodynamic pressure monitoring system as recited in claim 13 wherein the trifurcated IV set comprises a needle having a lumen extending therethrough; a drip chamber connected to the needle; first resilient tubing connected to the drip chamber; a four port connector attached to the resilient tubing; second, third and fourth resilient tubing connected respectively to the remaining three ports of the four port connector and each connected to a flush valve.

15. A hemodynamic pressure monitoring system as recited in claim 12 wherein the base comprises an apertured base in which the apertures cooperate with the first, second and third flush valves for mounting the flush valves on the base.

16. A hemodynamic pressure monitoring system as recited in claim 15 wherein actuating means provided on the flush valves for flushing the valves upon compression extend through the apertures to mount the flush valves on the base.

* * * * *